United States Patent [19]

Stautzenberger

[11] Patent Number: 4,760,166

[45] Date of Patent: Jul. 26, 1988

[54] PURIFICATION OF DIPHENYL PHTHALATES

[75] Inventor: Adin L. Stautzenberger, Corpus Christi, Tex.

[73] Assignee: Hoechst Celanese Corporation, Chatham, N.J.

[21] Appl. No.: 84,263

[22] Filed: Aug. 11, 1987

[51] Int. Cl.$^4$ ............................................. C07C 67/48
[52] U.S. Cl. ....................................... 560/78; 560/86; 203/14; 203/88
[58] Field of Search ...................... 560/78, 86; 203/14, 203/88

[56] References Cited

U.S. PATENT DOCUMENTS

| | | | |
|---|---|---|---|
| 2,197,546 | 4/1940 | Baxter et al. | 560/78 |
| 2,780,643 | 2/1957 | Buchner et al. | 560/78 X |
| 3,597,470 | 8/1971 | Witt et al. | 560/79 |
| 3,705,186 | 12/1972 | Naskar et al. | 560/78 |
| 4,118,582 | 10/1978 | Walker | 560/96 |
| 4,349,688 | 9/1982 | Sandler | 560/91 |

*Primary Examiner*—Werren B. Lone
*Assistant Examiner*—Vera C. Clarke
*Attorney, Agent, or Firm*—Depaoli & O'Brien

[57] ABSTRACT

Color properties of crude phenolic esters of aromatic dicarboxylic acids are improved by comminuting the ester to a finely divided particle size in the presence of an aqueous or alcoholic alkali solution and thereafter distilling the esters to obtain phenolic esters of reduced color.

6 Claims, No Drawings

PURIFICATION OF DIPHENYL PHTHALATES

BACKGROUND OF THE INVENTION

1. Field of the Invention

The present invention relates to the purification of phenolic esters of aromatic carboxylic acids and more particularly to the purification of diphenyl esters of aromatic carboxylic acids, such as phthalic acid, isophthalic acid, etc., to provide ester monomers having good color properties.

2. Description of the Prior Art

The production of various phenolic esters of aromatic benzenedicarboxylic acids, such as diphenyl terephthalate, have become of significant commercial interest in recent years due to their use in a great many types of processes. As an example, diphenyl terephthalate and diphenyl isophthalate when dissolved in a solvent may be reacted with a primary diamine to produce polyamides. Likewise, 3,3′-diaminobenzidine may be condensed with various diphenyl esters to form polybenzimidazoles. In the synthesis of polyarylate resins, such as Durel ®, a mixture of iso- and terephthalates is reacted with bisphenol-A to provide resins which are of significant commercial interest. These esters may be produced by reaction of acid chlorides with a phenol to produce the phenyl ester and hydrogen chloride as a by-product, or by reacting a phenolic compound and aromatic dicarboxylic acid in the presence of a catalyst consisting of an alkali metal compound and a boron compound or organic titanates or zirconates. While such processes are effective for producing phenolic esters they suffer the disadvantage that during the process of esterification, the ester acquires a grey to brown color which methods of purification, such as vacuum distillation, recrystallization and/or carbon treatment, are insufficient to remove. Accordingly, there is a need for additional purification methods which are sufficient to achieve specification grade diphenyl phthalates.

U.S. Pat. No. 2,197,546 discloses color improvement of phthalic acid esters such as dibutyl, dihexyl, dioctyl, etc., phthalates, by heating the ester with salts of perboric acid at reflux under reduced pressure followed by separation of the ester by filtration. U.S. Pat. No. 2,780,643 discloses catalytic hydrogenation of synthetic alcohols for color improvement, followed by esterification of the alcohol with phthalic acid. U.S. Pat. No. 3,597,470 discloses purification of bis(2-hydroxyethyl) terephthalate for color improvement by contacting the terephthalate with a solution of sodium borohydride or diborane followed by crystallization and separation. U.S. Pat. No. 4,118,582 discloses purification of spent recycle ethylene glycol, recovered from polyethylene terephthalate manufacture, by adding an organic acid (e.g., acetic acid) and an alkali metal borohydride in the absence of oxygen to precipitate antimony oxide which is used as a catalyst in preparing the polyethylene terephthalate.

A specific purification method is disclosed in U.S. Pat. No. 3,705,186 for producing pure, colorless diphenyl terephthalate. It begins with transesterification of dialkyl terephthalates with at least equivalent amounts of phenyl acetate in the presence of butyltitanate as a catalyst by (a) heating the dialkyl terephthalate with phenyl acetate in an inert atmosphere in the presence of 1–5 wt. % of activated carbon to temperatures above 150° C., (b) then adding the titanic acid ester, (c) immediately removing the alkyl acetate, (d) stirring the hot carbon-containing crude ester into a relatively high boiling aromatic hydrocarbon, such as xylene, under an inert gas, and (e) crystallizing the product after removing activated carbon by filtering.

SUMMARY OF THE INVENTION

The present invention is directed to the improvement of color properties in phenolic esters of aromatic carboxylic acids, especially the diphenyl esters, by comminuting the crude solid phenolic ester to a finely divided particle size in the presence of an aqueous or alcoholic alkali solution, separating and washing the comminuted ester free of alkali, and thereafter distilling the ester to obtain a phenolic ester of reduced color.

DESCRIPTION OF THE INVENTION

In carrying out the invention crude diphenyl esters such as diphenyl phthalate, diphenyl isophthalate, etc., are comminuted to a finely divided particle size of less than 50 microns, preferably a size of 2 to 30 microns, in the presence of an aqueous or alcoholic solution of an alkali. The use of the alkali solution neutralizes acid in the ester (free or monoester) and also serves to leach or wash the ester material free of color impurities. Preferred alkali solutions are sodium and potassium hydroxide which are used in an amount sufficient to neutralize acid in the ester, usually about a two-fold excess based on the acid number (mg KOH/g sample) of the ester. Alkali solutions of sodium carbonate, potassium carbonate, sodium bicarbonate, potassium bicarbonate, and the like, also may be used but are less preferred.

The preferred alkali solution is an alcoholic solution of potassium hydroxide in a lower alkanol having 1 to 4 carbon atoms, such as isopropanol or t-butanol. Alcoholic solutions such as of potassium hydroxide have been found to wet the solid ester material better than aqueous solutions, and are thus more effective penetrants.

Comminution of the crude diphenyl ester to a particle size of less than 50 microns requires no special type of apparatus and may be carried out in a ball mill, pebble mill, or other equivalent apparatus. To facilitate comminution, non-ionic surface active agents, such as alpha-[4-(1,1,3,3-tetramethylbutyl)phenyl]-omega-hydroxy-poly (oxy-1,2-ethanediol) may be added to the crude ester, if desired. Chelating agents such as versenic acid (EDTA) also may be employed for removal of metal impurities.

Comminution is carried out for a period of time sufficient to reduce the particle size of the crude ester to a finley divided size. In the examples shown hereinafter, the aqueous and alcoholic solutions of esters required about six hours of comminution in a pebble mill to obtain particle sizes within the range of 2 to 30 microns.

Following comminution of the aqueous or alcoholic solution of alkali, the resulting slurry is filtered to recover the ester filter cake which is then washed essentially free of ions, dried and vacuum distilled. Washing may be accomplished with water (preferably with distilled water and conveniently in the filter) or a lower alkanol of one to four carbon atoms such as isopropanol. After washing is complete, the filter cake is dried in a rotary drier or vented oven or preferably a vacuum oven at a temperature between about 25° C. and 150° C.

Flash distillation of the filter cake is thereafter carried out in a conventional manner at temperature of 225° C. to 260° C. under subatmospheric pressure of about 0.5 to 3 torr. Prior to flash distillation, $K_2CO_3$ or other alkali, as above noted, may be added to the ester in slight excess over any acidity (acid number) of the filter cake.

The advantages provided by the simplicity of the invention are several and diverse. Comminution of the ester, for example, can be carried out wet or dry depending on whatever is most practical. Recovery of the ester by flash distillation is relatively low cost as compared to purification processes involving multiple distillation, recrystallization, solvent extraction and saponification techniques. Additionally, the process of the invention avoids the handling of solvents and their attendant need for recycle which are costly in time, yield and environmental requirements.

The phenolic esters which are purified in accordance with the invention are derived from aromatic carboxylic acids which should be essentially free of aldehydic and ketonic carbonyl groups as these groups interfere with the esterification reaction. Other than these aldo and keto groups, the aromatic carboxylic acid may contain various functional groups which do not interfere with the esterification reaction. Generally the aromatic carboxylic acid will contain no functional groups or radicals other than carboxyl, carboxylic ester, ether, thioether, aromatic ring-substituted halo, sulfo, or sulfonyl. The aromatic carboxylic acids which are free of ketonic and aldehydic carbonyl groups have the formula:

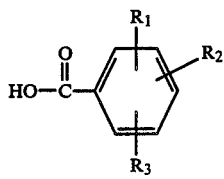

wherein $R_1$ and $R_2$ are alike or different and correspond to hydrogen, carboxyl or hydroxyl and wherein $R_3$ is hydrogen or an organic radical of six to 20 carbon atoms containing an aromatic ring, which organic radical is composed only of elements selected from the groups consisting of carbon, hydrogen, and oxygen.

Especially preferred are those dicarboxylic acids of the formula

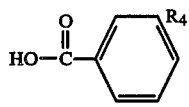

where $R_4$ is carboxyl group or a radical of seven to 20 carbon atoms of the formula

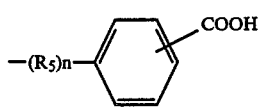

wherein n is 0 or 1 and $R_5$ is a divalent hydrocarbon radical, oxygen, or a divalent radical composed of carbon, hydrogen, and oxygen wherein the oxygen present is as an ether linkage. Among the acids containing aromatic ring-substituted carboxyl groups that are preferred are benzoic acid, phthalic acid, terephthalic acid, isophthalic acid, diphenic acid, homophthalic acid, toluic acid, alpha-naphthoic acid, chlorobenzoic acid, salicylic acid, 1,2-(ethylenedioxy)dibenzoic acid, and 2,5-dimethylterephthalic acid. Mixtures (3/1) of iso- and terephthalic acid are especially preferred.

The phenols utilized for production of the esters are monofunctional phenols which contain only one phenolic hydroxyl group. Generally these phenols will be those of six to 15 carbon atoms of the formula

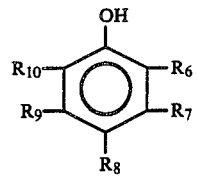

wherein $R_6$, $R_7$, $R_8$, $R_9$ and $R_{10}$ may be hydrogen, alkyl, alkaryl, aryl, or aralkyl radicals. Among the particular phenols that may be utilized are phenol, o-cresol, m-cresol, p-cresol, xylenols, either mixed or the pure isomer, o-phenylphenol, and p-phenylphenol. Of the various phenols that may be utilized, phenol itself is preferred over the others.

The reaction of the aromatic carboxylic acid with phenol in the presence of a catalyst is a known reaction which is carried out in the liquid phase in a customary manner using equipment normally used for esterification reactions. The organic carboxylic acid is reacted with an excess of the phenol. The reaction conditions can be varied depending upon the type of esters being formed and the particular phenol being employed. A temperature sufficient to effect esterification in the presence of the catalyst is used and generally at temperatures ranging between 230° C. and 300° C. Catalysts which may be employed for esterification include organotitanates, organozirconates and organostannates.

The following examples illustrate the best mode now contemplated for carrying out the invention.

EXAMPLE 1

The crude mixture of diphenyl iso- and terephthalates used in this experiment was tan colored and had an APHA color of much greater than 1000. The monomer had an acid number of 6.2 (mg KOH/g) and was prepared from phenol and 3/1 mixture of isophthalic acid and terephthalic acid in the presence of triethanolamine titanate chelate catalyst (Tyzor TE). 200 grams of the crude monomer was added to 500 ml of a 2 wt% aqueous solution of sodium hydroxide and one minidrop of a non-ionic surface active agent alpha-[4-(1,1,3,3-tetramethylbutyl)phenyl]-omega-hydroxy-poly (oxy-1,2-ethanediol).* The resulting slurry was charged to a 2-liter pebble mill and comminuted at room temperature for six hours. The slurry was filtered, leaving a yellow filtrate, water-washed and the filter cake was dried overnight in a vacuum oven at 65° C. The filter cake was light gray in color and had an acid number (mg KOH/g of sample) of 0.4. The filter cake was subject to vacuum flash distillation at a pressure of about 1 mm Hg at about 240° C. in the presence of 0.5 gram $K_2CO_3$ to yield a molten distillate having an APHA color of 150. Particle size of the ground material was 2 to 30 microns.
* TRITON X-100

EXAMPLE 2

A crude Durel ® monomer (crude diphenyl iso- and terephthalates) having an APHA color of much greater than 1000 was prepared from phenol and a 3/1 mixture of isophthalic acid and terephthalic acid in the presence of zirconium tetra-n-propoxide catalyst. 200 grams of the monomer was added to 500 ml of a 2 wt% aqueous solution of sodium hydroxide and one minidrop of a non-ionic surface active agent alpha-[4-(1,1,3,3-tetramethylbutyl)phenyl]-omega-hydroxy-poly (oxy-1,2-ethanediol).* The resulting slurry was charged to a 2-liter pebble mill and a comminuted at room temperature for six hours. The slurry was filtered and the filter cake was washed with water and dried overnight in a vacuum oven at 65° C. The filter cake had a gray-tan color, an acid number of 0.026, and was flash vacuum distilled at 2–0.5 torr at a temperature of about 240° C. in the presence of 0.5 gram $K_2CO_3$ to yield a molten distillate having an APHA color of 125. The particle size of the comminuted sample was 2 to 30 microns.
*TRITON X-100

EXAMPLE 3

The procedure of Example 2 was repeated using a 2 wt% solution of KOH in isopropyl alcohol instead of sodium hydroxide in water. The alcoholic alkali solution wets the solid material better than the aqueous alkali solution and appears more effective as a penetrant. The alcoholic leach solution was darker than the aqueous leach solution which indicates more color removal from the monomer solid. After vacuum flash distillation the molten distillate had an APHA color of 125.

What is claimed:

1. A method for purification of diphenyl esters of aromatic carboxylic acid which comprises the steps of:
    (a) forming a slurry of said ester with an aqueous or alcoholic solution of an alkali compound;
    (b) comminuting said slurry for a period of time sufficient to reduce the ester to a particle size of 50 microns or less;
    (c) recovering the ester from said slurry; and
    (d) distilling said ester under subatmospheric pressure at temperatures of about 225° C. to 260° C. to produce a phenolic ester of reduced color properties.
2. The method of claim 1 wherein said esters are diphenyl phthalates.
3. The method of claim 2 wherein the pressure is 0.5 to 3 torr.
4. The method of claim 3 wherein said esters are diphenyl phthalates which are prepared from the catalytic reaction of phenol with a 3/1 mixture of iso- and terephthalic acid.
5. The method of claim 4 wherein the aqueous or alcoholic solution is a solution of sodium or potassium or lithium hydroxide.
6. The method of claim 5 wherein the sodium or potassium hydroxide is present in a slight excess over the total acidity (acid number) of the ester.

* * * * *